US010279080B2

(12) United States Patent
Young et al.

(10) Patent No.: US 10,279,080 B2
(45) Date of Patent: May 7, 2019

(54) METHOD OF TREATING SPINAL DISK

(71) Applicant: SpineOvations, Inc., Carlsbad, CA (US)

(72) Inventors: Stuart Young, Del Mar, CA (US); Neville Alleyne, La Jolla, CA (US); Nicholas John Manesis, Escondido, CA (US)

(73) Assignee: SpineOvations, Inc., Carlsbad, CA (US)

( * ) Notice: Subject to any disclaimer, the term of this patent is extended or adjusted under 35 U.S.C. 154(b) by 0 days.

(21) Appl. No.: 15/636,446

(22) Filed: Jun. 28, 2017

(65) Prior Publication Data
US 2017/0296701 A1  Oct. 19, 2017

Related U.S. Application Data

(63) Continuation of application No. PCT/US2016/013718, filed on Jan. 15, 2016.

(60) Provisional application No. 62/104,632, filed on Jan. 16, 2015.

(51) Int. Cl.
| A61L 27/16 | (2006.01) |
| A61L 27/48 | (2006.01) |
| A61L 27/20 | (2006.01) |
| C08L 5/08  | (2006.01) |
| C08L 33/12 | (2006.01) |
| A61M 5/32  | (2006.01) |
| A61F 2/44  | (2006.01) |

(52) U.S. Cl.
CPC .............. A61L 27/48 (2013.01); A61L 27/16 (2013.01); A61L 27/20 (2013.01); A61M 5/329 (2013.01); C08L 5/08 (2013.01); C08L 33/12 (2013.01); A61F 2002/4435 (2013.01); A61L 2430/38 (2013.01); A61M 2210/02 (2013.01)

(58) Field of Classification Search
CPC ...... A61L 2430/38; A61L 27/16; A61L 27/20; A61L 27/48; A61M 2210/02; A61M 5/329

See application file for complete search history.

(56) References Cited

U.S. PATENT DOCUMENTS

| 2,474,911 | A | 7/1949 | Pierce et al. |
| 4,526,909 | A | 7/1985 | Urist |
| 4,837,285 | A | 6/1989 | Berg et al. |
| 5,024,659 | A | 6/1991 | Sjostrom |
| 5,134,122 | A | 7/1992 | Orsolini |
| 5,171,279 | A | 12/1992 | Mathews |
| 5,258,028 | A | 11/1993 | Ersek et al. |
| 5,286,763 | A | 2/1994 | Gerhart et al. |
| 5,290,271 | A | 3/1994 | Jernberg |
| 5,344,452 | A | 9/1994 | Lemperle |
| 5,352,715 | A | 10/1994 | Wallace et al. |
| 5,480,440 | A | 1/1996 | Kambin |
| 5,571,182 | A | 11/1996 | Ersek et al. |
| 5,599,852 | A | 2/1997 | Scopelianos et al. |
| 5,641,514 | A | 6/1997 | Cho |
| 5,922,025 | A | 7/1999 | Hubbard |
| 6,107,466 | A | 8/2000 | Hasan et al. |
| 6,160,033 | A | 9/2000 | Nies |
| 6,129,761 | A | 10/2000 | Hubbell |
| 6,183,518 | B1 | 2/2001 | Ross et al. |
| 6,264,650 | B1 | 7/2001 | Hovda et al. |
| 6,264,651 | B1 | 7/2001 | Underwood et al. |
| 6,264,659 | B1 | 7/2001 | Ross et al. |
| 6,264,695 | B1 | 7/2001 | Stoy |
| 6,284,872 | B1 | 9/2001 | Celeste et al. |
| 6,309,420 | B1 | 10/2001 | Preissman |
| 6,335,028 | B1 | 1/2002 | Vogel et al. |
| 6,355,705 | B1 | 3/2002 | Bond et al. |
| 6,383,200 | B1 | 5/2002 | Wotton, III |
| 6,391,059 | B1 | 5/2002 | Lemperle et al. |
| 6,432,437 | B1 | 8/2002 | Hubbard |
| 6,468,274 | B1 | 10/2002 | Alleyne et al. |
| 6,500,180 | B1 | 12/2002 | Foley |
| 6,602,248 | B1 | 8/2003 | Sharps et al. |
| 6,652,883 | B2 | 11/2003 | Goupil et al. |
| 6,713,527 | B2 | 3/2004 | Bond et al. |
| 7,060,103 | B2 | 6/2006 | Carr et al. |
| 7,131,997 | B2 | 11/2006 | Bourne |
| 7,306,627 | B2 | 12/2007 | Tanagho et al. |

(Continued)

FOREIGN PATENT DOCUMENTS

| CN | 101502676 A | 8/2009 |
| EP | 1410810 B1 | 1/2007 |

(Continued)

OTHER PUBLICATIONS

Comparison chart [online] retrieved on Apr. 25, 2018 from: http://tru-flo.com/Technical/viscosity_chart.pdf; 1 page. (Year: 2018).*
Viscosity comparison chart [online] retrieved on Jul. 4, 2018 from: http://www.cstsales.com/viscosity.html; 1 page. (Year: 2018).*
English translation of CN101502676B (published Aug. 12, 2009) 16 pages. (Year: 2009).*
Bergeret-Galley et al. (Aesthetic Plastic Surger; 2001;25:249-255) (Year: 2001).*
English Abstract to CN101502676A Aug. 12, 2009 ; 2 pages. (Year: 2009).*

(Continued)

Primary Examiner — Ernst V Arnold
(74) Attorney, Agent, or Firm — Veros Legal Solutions, LLP

(57) ABSTRACT

A method of treating a spinal disk according to the present invention can include inserting an alloplastic bulking agent into the spinal disk to treat the defect. The alloplastic bulking agent has a plurality of microparticles and a suspending agent comprising hyaluronic acid. The bulking agent results in at least one of sealing the defect, increasing a pressure of the disk, increasing a height of the disk, improving stability of the disk and improving structural integrity of the disk.

10 Claims, 2 Drawing Sheets

(56) References Cited

U.S. PATENT DOCUMENTS

| | | |
|---|---|---|
| 7,341,601 B2 | 3/2008 | Eiserman et al. |
| 7,442,389 B2 | 10/2008 | Quelle et al. |
| RE41,286 E | 4/2010 | Atkinson et al. |
| 8,127,770 B2 | 3/2012 | Alleyne et al. |
| 8,398,638 B2 | 3/2013 | Alleyne et al. |
| 8,586,089 B2 | 11/2013 | Anderson |
| 2002/0045942 A1 | 4/2002 | Ham |
| 2002/0120259 A1 | 8/2002 | Lettice |
| 2002/0176893 A1 | 11/2002 | Wironen et al. |
| 2003/0009235 A1 | 1/2003 | Manrique et al. |
| 2003/0014051 A1 | 1/2003 | Woloszko |
| 2003/0040742 A1 | 2/2003 | Underwood et al. |
| 2003/0149490 A1 | 8/2003 | Ashman |
| 2003/0158545 A1 | 8/2003 | Hovda et al. |
| 2003/0158607 A1 | 8/2003 | Carr et al. |
| 2003/0211083 A1 | 11/2003 | Vogel |
| 2003/0212395 A1 | 11/2003 | Woloszko et al. |
| 2003/0236573 A1 | 12/2003 | Evans et al. |
| 2004/0010317 A1 | 1/2004 | Lambrecht et al. |
| 2004/0024465 A1 | 2/2004 | Lambrecht et al. |
| 2004/0054414 A1 | 3/2004 | Trieu et al. |
| 2004/0091540 A1 | 5/2004 | Desrosiers et al. |
| 2004/0115240 A1 | 6/2004 | Narhi et al. |
| 2004/0127963 A1 | 7/2004 | Uchida et al. |
| 2005/0031666 A1 | 2/2005 | Trieu |
| 2005/0100510 A1 | 5/2005 | Falco |
| 2006/0002971 A1 | 1/2006 | Saltzman et al. |
| 2006/0052795 A1 | 3/2006 | White |
| 2006/0074424 A1 | 4/2006 | Alleyne et al. |
| 2006/0093644 A1 | 5/2006 | Quelle et al. |
| 2006/0206116 A1 | 9/2006 | Yeung |
| 2006/0263830 A1 | 11/2006 | Grinstaff et al. |
| 2007/0093907 A1 | 4/2007 | Goupil et al. |
| 2007/0168038 A1 | 7/2007 | Trieu |
| 2008/0096976 A1 | 4/2008 | Alleyne |
| 2008/0124371 A1 | 5/2008 | Turos et al. |
| 2008/0160060 A1 | 7/2008 | Ellies |
| 2008/0166386 A1 | 7/2008 | Caseres et al. |
| 2008/0299172 A1 | 12/2008 | Young et al. |
| 2009/0074728 A1 | 3/2009 | Gronthos et al. |
| 2010/0004699 A1 | 1/2010 | Alleyne et al. |
| 2010/0004700 A1 | 1/2010 | Alleyne |
| 2010/0010549 A1 | 1/2010 | Alleyne et al. |
| 2010/0041788 A1 | 2/2010 | Voigts et al. |
| 2010/0172829 A1 | 7/2010 | Anderson |
| 2010/0316715 A1 | 12/2010 | Andersson |
| 2011/0230919 A1 | 9/2011 | Alleyne |

FOREIGN PATENT DOCUMENTS

| | | |
|---|---|---|
| JP | 5-508795 | 12/1993 |
| JP | 2002-505308 | 2/2002 |
| WO | WO 92/10982 | 7/1992 |
| WO | WO 98/40113 | 9/1998 |
| WO | WO 99/44643 | 9/1999 |
| WO | WO 2000/044394 | 8/2000 |
| WO | WO 2000/044808 | 8/2000 |
| WO | WO 0168721 | 9/2001 |
| WO | WO 2002/040070 | 5/2002 |
| WO | WO 2002/062404 | 8/2002 |
| WO | WO 2003/049669 | 6/2003 |
| WO | WO 2004/026189 | 4/2004 |
| WO | WO 2005/046746 | 5/2005 |
| WO | WO 2008/005676 | 1/2008 |
| WO | WO 2009/155656 A1 | 12/2009 |

OTHER PUBLICATIONS

English translation of CN101426451B Dec. 13, 2006; 6 pages. (Year: 2006).*

Kim et al. (Macromolecular Research 2009;17(4):250258) (Year: 2009).*

Bayston, et al., "The sustained release of antimicrobial drugs from bone cement. An appraisal of laboratory investigations and their significance," J. Bone Joint Surg. (Br), (1982) 64(4):460-464.

Carruthers, Artecoll®—an injectable micro-implant for longlasting soft tissue augmentation, Skin Therapy Letter, (1999), vol. 4(2), 1-2.

Cohen et al., Artecoll—A Long-Lasting Injectable Wrinkle Filler Material: Report of a Controlled, Randomized, Multicenter Clinical Trial of 251 Subjects, Plastic Reconst. Surg., (2004) vol. 114(4), 964-976.

Faught, W.E. and Lawrence, P.F. "The effects of laser energy on the arterial wall." Annals of Vascular Surgery 4 (1990); 198-207.

Lautenschlager, "Hyaluronic Acid—A Legendary Agent" Kosmetische Praxis 2008 (4), 16-18.

Masala, et al., Percutaneious Vertebroplasty in Painful Schmorl Nodes, Published Online Nov. 18, 2005, Cardiovasc Intervent Radiol 29:97-101.

Omlor, G. W. et al. Injection of a polymerized hyaluronic acid/collagen hydrogel matrix in an in vivo porcine disc degeneration model. European, Spine Journal, 2012, vol. 21, pp. 1700-1708.

Sundaram et al., "Comparison of the Rheological Properties of Viscosity and Elasticity in Two Categories of Soft Tissue Fillers: Calcium Hydroxylapatite and Hyaluronic Acid" Dermatol Surg 2010; 36:1859-1865.

Wahlig, et al., "Pharmacokinetic study of gentamicin-loaded cement in total hip replacements. Comparative effects of varying dosage," J. Bone Joint Surg. (Br), (1984) 66(2):175-179.

International Search Report in application for International Application No. PCT/US2016/013718, dated Jun. 22, 2016.

* cited by examiner

METHOD OF TREATING SPINAL DISK

CROSS-REFERENCE TO RELATED APPLICATIONS

This application is a continuation of PCT Application No. PCT/US2016/013718, filed Jan. 15, 2016, which claims priority to U.S. Provisional Patent Application Ser. No. 62/104,632, filed on Jan. 16, 2105 and entitled "Method of Treating Spinal Internal Derangement." Each of the above applications is hereby incorporated by reference in its entirety.

BACKGROUND OF THE INVENTION

Field of the Invention

The present invention relates generally to surgical implants and, more particularly, relates to alloplastic spinal disk implants and procedures.

Description of the Related Art

Spinal disks comprise a central region called the nucleus pulposus surrounded by a second region known as the annulus fibrosis. The annulus fibrosis portion comprises collagen fibers that may weaken, rupture, or tear, leading to compromised annular confinement of the nucleus and producing disk bulges, herniations and other disk pathologies. The major causes of persistent, often disabling, back pain are disruption of the spinal disk annulus fibrosis, chronic inflammation of the spinal disk (e.g., herniation), or relative instability of the vertebral bodies surrounding a given spinal disk, such as the instability that often occurs due to a degenerative disease. In some cases, the spinal disk tissue is irreparably damaged, thereby necessitating surgical removal of a portion of the spinal disk or the entire spinal disk to eliminate the source of inflammation and pressure. Following removal, spinal disks may contain annular defects or openings that can increase the possibility of recurrent complications such as, for example, future nuclear herniations.

Some methods to treat such defects focus on injecting compositions containing collagen based suspending agents into an affected spinal disk. For example, U.S. Pat. No. 8,398,638 discloses a composition including microparticles suspended in a collagen suspending agent, and teaches that such a composition can be utilized to treat a damaged spinal disk. Similarly, U.S. Pat. No. 8,586,089 describes a composition of microparticles and a biocompatible carrier medium in the form of cross-linked collagen and biocompatible gelatin for treating a patient's tissue or fluids. It is directed to adjusting the ratio of cross-linked collagen in the biocompatible carrier medium in order to improve the viscosity of the composition. More specifically, U.S. Pat. No. 8,586,089 is directed towards using cross-linked collagen in a biocompatible carrier medium in order to improve "resistance to deformation," "shear modulus," and "dynamic viscosity," as well as to allow injection without excessive force.

SUMMARY OF THE INVENTION

In accordance with one aspect of the present invention, methods are provided for treating and sealing invertebrate spinal disks that have tears or fissures on the annulus fibrosus.

In one embodiment, a method of treating a spinal disk comprises delivering an agent to the spinal disk, wherein the agent comprises a plurality of microparticles and hyaluronic acid.

In another embodiment, a medical kit comprises an agent comprising microparticles and hyaluronic acid and one or more surgical tools configured for repairing at least one spinal disk.

In another embodiment, an implant agent comprises a plurality of microparticles and hyaluronic acid, for use in repairing and/or improving structural integrity of spinal disks.

In addition, a method of treating a spinal disk comprises placing a plurality of particles into an interior portion of the spinal disk.

DETAILED DESCRIPTION OF THE INVENTION

Figure 1:
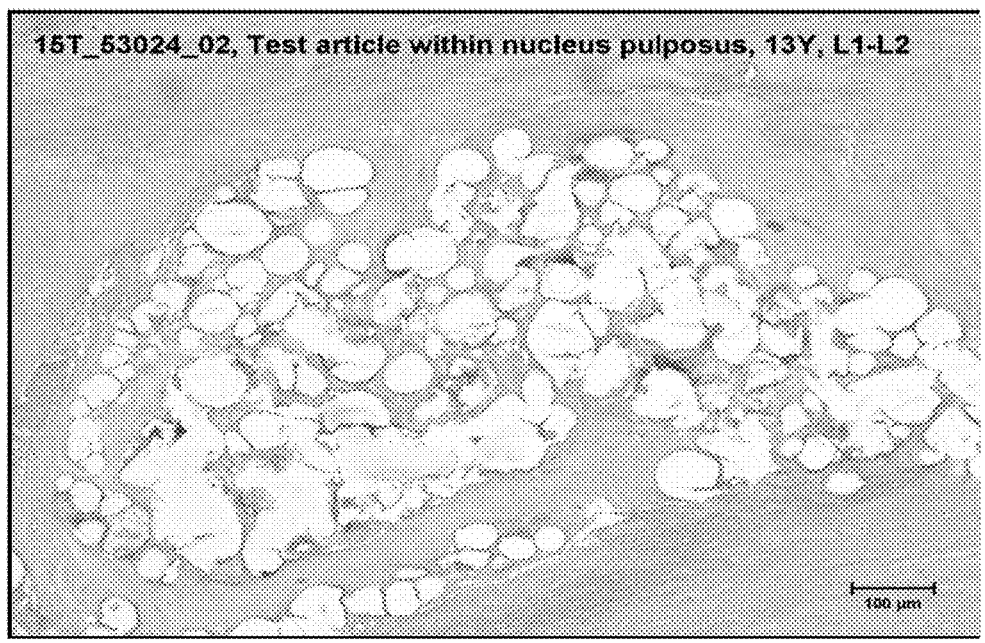
FIG. 1 depicts a test article within a nucleus polposus of intervertebral disc sections L1-L2 of a test animal 13Y.

Any feature or combination of features described herein are included within the scope of the present invention provided that the features included in any such combination are not mutually inconsistent as will be apparent from the context, this description, and the knowledge of one skilled in the art. In addition, any feature or combination of features may be specifically excluded from any embodiment of the present invention. For purposes of summarizing the present invention, certain aspects, advantages and novel features of the present invention are described herein. Of course, it is to be understood that not necessarily all such aspects, advantages or features will be embodied in any particular embodiment of the present invention.

In reference to the disclosure herein, for purposes of convenience and clarity only, directional terms, such as, top, bottom, left, right, up, down, upper, lower, over, above, below, beneath, rear, and front, may be used. Such directional terms should not be construed to limit the scope of the invention in any manner. It is to be understood that embodiments presented herein are by way of example and not by way of limitation. The intent of the following detailed description, although discussing exemplary embodiments, is to be construed to cover all modifications, alternatives, and equivalents of the embodiments as may fall within the spirit and scope of the invention.

The present invention provides compositions and methods for selectively treating defects within or on a spinal disk. These procedures include laminectomy/diskectomy procedures for treating herniated spinal disks, decompressive laminectomy for stenosis in the lumbosacral and cervical spine, medial facetectomy, posterior lumbosacral and cervical spine fusions, treatment of scoliosis associated with vertebral disease, foraminotomies to remove the roof of the intervertebral foramina to relieve nerve root compression and anterior cervical and lumbar discectomies. These procedures may be performed through open procedures (e.g., laminotomy, laminectomy, hemilaminotomy and hemilaminectomy), or using minimally invasive techniques, such as thoracoscopy, arthroscopy, laparoscopy, diskogrophy (e.g., performed percutaneously through a posterior, posterolateral, lateral, anterior or anterolateral approach to the spinal disk) or the like.

In accordance with an aspect of the present invention, a biocompatible alloplastic implant is provided for sealing tears or other defects or conditions of a spinal disk, such as a rent in the annulus fibrosis of a spinal disk. The biocompatible alloplastic implant can be inserted into a ruptured spinal disk, filling a portion of the nucleus pulposus and/or annulus fibrosis and providing a seal. In one implementation, the biocompatible alloplastic implant is inserted into a center region of the ruptured spinal disk. According to certain aspects, the biocompatible alloplastic implant is inserted into the nucleus pulposus after a microdiscectomy which closes the iatrogenic rent or annulotomy that the surgeon creates thereby minimizing the risk for recurrent herniation, or is administered as an injectable sealant into the center of the spinal disk, for example, after a diskography procedure in order to seal one or more annular tears.

To the extent such tears or defects are treated using the present invention, risks for recurrent spinal disk herniations and possible revision surgeries can be attenuated or eliminated. Such revisions typically entail slightly larger incisions, greater bony resection, removal of scar tissue, more difficult retraction, increased bleeding, increased anesthetic time, and increased risk for battered nerve roots or possible injury to the dura or root sleeves resulting in potential Cerebro-Spinal Fluid (CSF) leak, fistula, infection, etc. As a result of the minimized need for revision surgery, surgical outcome can be improved and the need for repeat surgery at the same level can be decreased.

Moreover, with the perhaps increased use of provocative diskography to ascertain, for example, whether adjacent segments above or below a planned fusion need to be incorporated, a user can instill the biocompatible alloplastic implant to minimize the extension of the fusion to the adjacent segment. Using conventional procedures, for example, if an unstable motion segment were planned to be fused and preoperative provocative diskography revealed the adjacent segment (e.g., the adjacent spinal disk) as also being symptomatic, that level would be included in the fusion mass. However, in accordance with an aspect of the present invention, the biocompatible alloplastic implant of the present invention can be instilled into the adjacent segment prior to the surgery to help seal the annular tear or tears. In one implementation, the biocompatible alloplastic implant of the present invention can be instilled into the adjacent segment during the preoperative provocative diskography. As a result, the use of the present biocompatible alloplastic implant is not limited to microdiscectomy or open diskectomy procedures, but can also be used for closed procedures in which, for example, imaging studies have proven that there are annular tears or rents which reproduce concordant pain. Installation of the biocompatible alloplastic implant, in accordance with one implementation of the present invention, may be especially suited for annular tears which are not asymptomatic and which do not produce discordant pain.

Implantation of the biocompatible alloplastic implant, if performed in the context of a closed procedure, can be accomplished from a posterior midline or posterolateral approach or a direct lateral approach. If performed in the context of an open procedure, implantation of the biocompatible alloplastic implant can be achieved from a posterior midline approach, posterolateral approach, anterior, anterolateral, or direct lateral approach. It is therefore possible that if an anterior approach is being utilized for an anterior diskectomy alone, the biocompatible alloplastic implant of the present invention can be instilled through a syringe and needle into that nucleus pulposus space after, for example, an offending spinal disk fragment or fragments have been removed. In certain implementations, the material can be introduced via flexible catheters of variable length and diameter, such as, for example, standard percutaneous needles and standard catheter tips known in the industry. In an exemplary open procedure where for example a laminectomy or microdiscectomy is being performed, it may be easier to inject the biocompatible alloplastic implant as used according to the present invention with the aid of an injection syringe, such as an syringe with a 3 or 4" 18-gauge needle. In representative embodiments, the size of the needle can range from 14-gauge to 26-gauge, from 18-gauge to 25-gauge, or from 20-gauge to 24-gauge, or 22 to 26 gauge. In certain implementations the size of the needle may be 20 gauge or smaller, 21 gauge or smaller, or 22-gauge or smaller. These gauge classifications correspond to industry standard inner and outer diameters, with an 18 gauge needle having an outer diameter of less than 1300 microns (nominally 1270 microns) and an inner diameter of less than 900 microns (nominally 838 microns). Needles in the 22 to 26 gauge range correspond to outer diameters of between 750 and 450 microns, and inner diameters between 450 and 240 microns. In some embodiments, the injection syringe may include a needle having a length of at least 3 inches, at least 5 inches, at least 6 inches, or at least 8 inches. In some embodiments, the needle comprises a pencil point needle. A pencil point needle can create a smaller perforation in the annulus fibrosis, which can limit extrusion of the biocompatible alloplastic implant through the perforation. Smaller perforations may also improve patient comfort. Larger perforations in the dura, such as those created with an 18-guage needle, can lead to head and neck pain in a patient, such as a headache. A needle causing a smaller perforation, such as a 25-gauge needle, may decrease the risk of such pain.

The maturation of the biocompatible alloplastic implant of the present invention, in accordance with an aspect of the present invention, can over time afford additional, or at least partial, stabilization to the annulus fibrosis which can then provide additional support to the motion segment involved. This change in the biomechanics can translate into a partial increase in the stability for this motion segment. Having an annular tear generally can cause a weakening in the supporting structure of the motion segment. Treating the nucleus pulposus of a spinal disk with the biocompatible alloplastic implant of the present invention can in certain implementations allow a maximum amount of the nuclear material to remain centrally located and/or can increase the integrity of the surrounding annular fibers.

The biocompatible alloplastic implant of the present invention preferably comprises a plurality of microparticles and a suspending agent. The suspending agent preferably comprises hyaluronic acid. Hyaluronic acid is a naturally occurring biodegradable polymer. It can be found in the extracellular matrix of all animal tissue, and is involved in several biological functions. Hyaluronic acid provides mechanical features to body tissue. It also has a role in regulating cell adhesion and cell motility. Furthermore, hyaluronic acid is involved in manipulating cell differentiation and proliferation. In some embodiments, the hyaluronic acid is in powder form prior to solubilization. In other embodiments, the hyaluronic acid may be in fiber form or cake form prior to solubilization. The suspending agent can further comprise at least one of water and saline. Furthermore, the suspending agent can be admixed with a tenside, such as Tween ad, since such a tenside changes the surface tension of water so that the microparticles have a more uniform distribution. The suspending agent may also include sterile Phosphate Buffered Solution (PBS). In certain implementations, the concentration of hyaluronic acid in PBS is at most 1.8%. The concentration of hyaluronic acid in PBS can be between 1.0% and 3.0% or 1.6% and 2.4%, In certain implementations, the concentration of hyaluronic acid in PBS may be 1.2%.

While previous attempts to treat damaged spinal disks have focused on collagen based suspending agents, a biocompatible alloplastic implant including a suspending agent with hyaluronic acid has many advantages over a suspending agent utilizing collagen. Hyaluronic acid is highly hydrophilic, which allows it to occupy a large volume relative to mass. The hydrophilic nature of hyaluronic acid further allows for the binding of water molecules to a suspending agent with hyaluronic acid in order to increase the viscosity of the biocompatible alloplastic implant. The suspending agent comprising hyaluronic acid can bind water molecules, thus increasing viscosity, after insertion into the interior of a spinal disk. Generally, a higher viscosity composition will require a larger needle and greater force, so increasing viscosity after injection allows for a wider range of needles to be used for injection. Furthermore, increasing viscosity after injection can prevent extrusion through the perforation created by the needle in the spinal disc. Hyaluronic acid is also capable of forming gels at low concentrations and can withstand compressive forces when water is drawn into the hyaluronic acid matrix. Hyaluronic acid also demonstrates no tissue or species specificity, which allows for minimal immune response or rejection such as that which can occur when using traditional suspending agents comprising collagen.

Previous attempts to improve treatment with collagen based implants have focused on improving the viscosity of a suspending agent by altering the ratio of cross-linked collagen in the suspending agent. In comparison to a collagen based suspending agent, the viscosity of a suspending agent comprising hyaluronic acid is more favorable for injection into and treatment of a damaged spinal disk. The viscosity of a suspending agent comprising hyaluronic acid can also be more readily adjusted than one containing collagen. Such an adjustment can be accomplished by changing the molecular weight, the concentration, or the amount of cross-linking of hyaluronic acid in the suspending agent. These properties are separately adjustable, allowing for improved control of the viscosity of the suspending agent in accordance with patient needs. At high concentrations, hyaluronic acid can have a stiff, viscous quality, like that of gelatin. At the same time, the shear modulus of hyaluronic acid also allows for injection using a thin needle. These properties allow for injection of an implant that provides improved structural integrity without requiring a larger perforation or increased force. In representative embodiments, the viscosity of the suspending agent with hyaluronic acid can range from 20,000 to about 350,000 centipoise, advantageously between 50,000 and 200,000 centipoise. Hyaluronic acid may also be cross-linked to increase the viscosity of a biocompatible alloplastic implant. The more highly cross-linked the hyaluronic acid, the greater the viscosity. While hyaluronic acid can have a high rate of elimination and turnover, these properties can be overcome through modification and cross-linking. Greater amounts of cross-linking can impede degradation, increasing the lifespan of a biocompatible alloplastic implant comprising hyaluronic acid. The concentration of hyaluronic acid in a suspending agent will also affect lifespan of a biocompatible alloplastic implant, with higher concentrations of hyaluronic acid leading to longer lifespans. Thus, the elimination and turnover time may be controlled to correspond to the needs of the patient. In some embodiments, the biocompatible alloplastic implant may have a shelf life of at least 12 months when stored between 2° to 8° C. or at room temperature. In certain implementations, the biocompatible alloplastic implant may have a shelf life of at least 18 months when stored between 2° to 8° C. or at room temperature.

The viscous properties of hyaluronic acid may also act to prevent extrusion from the perforation created during the injection of a biocompatible alloplastic implant. The hydrophilic nature of hyaluronic acid causes it to bind water molecules until completely saturated. Injection of a biocompatible alloplastic implant containing hyaluronic acid that is not completely saturated allows for the suspending agent to bind to more water molecules after placement in the interior of a spinal disc. When hyaluronic acid binds to water molecules in the interior of a disc, the viscosity and volume of the material inside the disk can increase, and consequently, prevent extrusion from occurring through the needle perforation created upon injection.

The annulus fibrosus measures radially between 6 mm to 8 mm. The annulus fibrosus includes a plurality of collagen layers (laminae), ranging between 15 to 40 layers. A needle introduced into the nucleus pulposus traverses the collagen layers. The needle may include a stylet such that introduction of the needle into the annulus fibrosis causes a majority of the annular fibers to be compressed rather than cut, which in turn prevents the incidental removal of tissue as a result of the injection process. When the needle is removed following injection, the perforated tissue may at least partially contract. For example, a 22-gauge needle has an outer diameter of approximately 700 microns. Upon removal of the 22-gauge needle, the perforation in the layers of the annulus fibrosis will have a diameter of approximately 350 microns or less. When the needle is removed, the layers of collagen may readjust such that the perforations through at least some of the layers may be offset. Furthermore, the layers of collagen are cross hatched and have adhesive properties. For extrusion to occur, an implant would have to traverse each collagen layers. In response to an axial load, a material having a low viscosity may extrude through each collagen layers, but a high viscosity material, such as a biocompatible alloplastic implant including hyaluronic acid may resist extrusion. In some embodiments, such a material may include microspheres having an average diameter of about 70 microns.

The concentration of hyaluronic acid in a suspending agent can affect the saturation level. A higher concentration of hyaluronic acid will require more water molecules to become completely saturated. Thus, the concentration of hyaluronic acid in a suspending agent can be adjusted to change the amount of saturation as desired. In representative embodiments, the concentration of hyaluronic acid in a suspending agent can range from 12-50 mg/ml. Concentrations above 20 mg/ml can bind large amounts of water, and consequently, may be favorable for preventing extrusion from occurring.

In representative embodiments, the average molecular weight of hyaluronic acid may be at least 1.6 M Da, at least 2.8 M Da., or at least 3 M Da. In some embodiments, the biocompatible alloplastic implant can be extruded using an extrusion force between 10 N to 30 N. Hyaluronic acid is a shear thinning polymer. A higher molecular weight of hyaluronic acid also has a greater shear thinning effect. Higher molecular weights of hyaluronic acid also may last longer in the body following implantation. Degradation in vivo may be enzymatic or due to applied forces. This degradation can occur by cleaving of low molecular weight fragments from a polymer chain. Use of higher molecular weight hyaluronic acid will cause larger sections of polymer to remain after cleaving, improving the amount of time the implant can last in vivo. Furthermore, degradation of a biocompatible alloplastic implant having 3 M Da molecular weight hyaluronic acid results in a material that still has an appreciable viscosity. In some embodiments, the hyaluronic acid may have a purity of greater than 95%. The moisture percentage of the hyaluronic acid may be between 8% to 15%. In some embodiments, the moisture percentage of the hyaluronic acid may be less than 20%.

The biocompatible alloplastic implant of the present invention preferably comprises a plurality of microparticles, which can comprise solid microparticles in representative embodiments. The plurality of microparticles can comprise one or more of poly methacrylate, polymethylmethacrylate (PMMA), a cured polymer, a fully polymerized polymer, and glass. PMMA microspheres may be linear (uncross-linked) or cross-linked. Cross-linked PMMA may be less brittle than non cross-linked PMMA, and thus more resilient and less prone to fracture under loads or weight. In modified implementations, the microparticles may not be altogether solid, such as implementations involving hollow or porous microparticles. The biocompatible alloplastic implant can in one implementation comprise a histocompatible solid in the form of a powder. The microparticles forming the solid may be incorporated into a suspending agent comprising hyaluronic acid. As used herein, the term "microparticles" refers to microparticles (e.g., in a dust or powder form) possessing an average diameter of 500 microns or less. Typically, the average diameter will be greater than about 20 microns rendering the microparticles too large to be "eaten" by monocytes. The microparticles can have diameters sufficient to keep them from being washed away through lymph tracts or other tissue tracts from the implantation site. If the microparticles do not have a spherical form, then the diameter as used herein refers to the greatest diameter of the smallest cross sectional area. It is, however, also possible to use smaller microparticles ranging from 4 to 5 microns or 5 to 10 microns in diameter. In representative embodiments, the microparticles can have an average diameter of about 15 to about 300 microns, about 15 to 250 microns, about 40 to 300 microns, about 20 to 250 microns, about 80 to 180 microns, about 40 microns to 110 microns or about 50 to about 100 microns. Use of hyaluronic acid in a suspending agent allows for the larger average diameters of the microparticles in some implementations, those ranging from about 80 to 300 microns, than would a suspending agent comprising collagen. In representative configurations, the microparticles are small enough to be injected through a fine gauge cannula (e.g., 18 gauge) or an injection syringe to the desired spinal disk region. Particles having the diameters specified herein may have a relatively minimal effect on the surrounding tissues, i.e., the dura of the cal sac or nerve root sleeves.

In some embodiments, linear or uncross-linked PMMA microspheres may have a glass transition temperature (Tg) of 105° C. This glass transition temperature can cause the PMMA microspheres to lose sphericity and mechanical properties when in contact with temperatures used for autoclaving (approximately 120° C.). Cross-linked PMMA microspheres have a higher glass transition temperature, which can make a biocompatible alloplastic implant more stable to thermal and mechanical exposure. In some embodiments, the PMMA may be cross-linked to an amount sufficient to have a glass transition temperature of 120° C. or greater. In some implementations, the PMMA may be cross-linked to an amount sufficient to have a glass transition temperature of 135° C. or greater. In some implementations, the PMMA may be cross-linked to an amount sufficient to have a glass transition temperature of 130° C. or greater. Cross-linked PMMA microspheres may include a cross-linking agent. The cross-linking agent may include ethylene glycol dimethacrylate which can be less than 1% (w/w) of the concentration of the biocompatible alloplastic implant.

Due to the formed surface and size of the microparticles used, they are not detected by the endogenous macrophages as foreign bodies so that no defensive reaction takes place. According to a representative embodiment, the microparticles have spherical forms or spherical-like forms capable of forming closely-packed arrangements at the site where they have been implanted and further capable of being individually encapsulated by the scar tissue.

The microparticles can be histocompatible with smooth surfaces free from corners and edges, can be dynamically balanced, and can have at least one of elliptical and spherical forms. For example, the plurality of microparticles typically can comprise a plurality of microspheres, which can be inserted into the spinal disk as loose microparticles and remain therein as loose microparticles.

In representative embodiments of the present invention, the biocompatible alloplastic implant can comprise 20-60% microspheres. In some embodiments, the biocompatible alloplastic implant comprising 20-60% microspheres can also comprise a suspending agent containing hyaluronic acid with a concentration ranging from 20-50 mg/ml. Combining a concentration of hyaluronic acid within the 20-50 mg/ml range with a percentage of microspheres in the 20-60% range can result in a biocompatible alloplastic implant that can be injected through a 22-23 gauge needle but will not extrude through the perforation created by the needle due to increased volume and viscosity after binding to water molecules in the interior of the spinal disc. In some embodiments, the biocompatible alloplastic implant can comprise 25-75% microspheres.

In some embodiments, the biocompatible alloplastic implant can comprise between 25% to 50% (w/w) PMMA, 30% to 50% (w/w) PMMA, 38% to 50% (w/w) PMMA, 38% to 48% (w/w) PMMA, 38% to 44% (w/w) PMMA, 38% to 42% (w/w) PMMA, 43% to 44% (w/w) PMMA, or 40% to 50% (w/w) PMMA. In some embodiments, the PMMA may have a purity of at least 95%.

In representative embodiments of the present invention, the plurality of microparticles can comprise PMMA microspheres. Use of PMMA can create a lower adhesive force and coefficient of friction than other polymers traditionally used in biocompatible implants like silicone. As explained above, more highly cross-linked and higher concentration hyaluronic acid suspending agents are desirable to bind with water on the interior of the disc after injection. However, the increased viscosity of such suspending agents can require the use of larger needles for injection. The use of PMMA microspheres can reduce the adhesive force and coefficient of friction present in the biocompatible alloplastic implant, allowing for injection using a smaller needle, thus creating a smaller perforation for possible extrusion.

It is one aspect of the material and methods described herein that the material can be injected into the disk by a physician with a relatively small needle, but the material does not extrude from the perforation in the patient left by the needle after injection. This is accomplished with embodiments of the invention without the use of any gelling or setting agents in the implant material that cause the material to polymerize, gel, or otherwise harden in place after injection through the annulus. Therefore an implant of simple composition can be used, reducing the risk of adverse reactions or complications following injection.

During a conventional provocative CT diskography, opening spinal-disk pressures are often measured. In the context of diskography, or any of the above-mentioned procedures, it is possible in accordance with certain aspects of the present invention for a spinal-disk opening pressure to be significantly altered by the introduction of the biocompatible alloplastic implant into the nucleus pulposus of that spinal disk and, preferably, into a central region of the nucleus pulposus, so that, for example, at least partial sealing of the spinal disk can be effectuated from the inside out.

As a result of implantation of the biocompatible alloplastic implant into a spinal disk, a seal or occlusion can be formed in the annulus fibrosis defect via, for example, in one implementation, displacement of nucleus pulposus from the site of implantation (e.g., an intermediate or, more preferably in some embodiments, central region of the nucleus pulposus) in a direction toward, for example, an annulus fibrosis defect, so that nucleus pulposus is displaced into a vicinity of the annulus fibrosis defect thus serving to strengthen or otherwise affect at least one property of the spinal disk or defect. In another implementation of the present invention, a seal or occlusion can be formed in the annulus fibrosis defect via, for example, introduction of the biocompatible alloplastic implant into the nucleus pulposus in a direct or proximate vicinity of the annulus fibrosis defect thus serving to enhance or otherwise affect at least one property of the spinal disk or defect. For instance, if the biocompatible alloplastic implant is injected or inserted in either a closed fashion or an open fashion, and if a sufficient portion of the biocompatible alloplastic implant is placed (and/or caused to solidify or mature) in the center, increased nuclear support can ensue giving rise to not only an increased annular integrity but also, for example, an increased nuclear stability.

Once placed into the nucleus pulposus, the biocompatible alloplastic implant may mimic or provide a substitute for at least one characteristic of the physiologic structure of the spinal disk. For example, the biocompatible alloplastic implant may mimic the spinal disk and operate as a partial artificial disk or operate as a partial artificial nucleus pulposus. Accordingly, a morphology of a disco gram may be improved following implantation of the biocompatible alloplastic implant. For instance, the accumulation of the microparticles of the biocompatible alloplastic implant and/or the accumulation of scar tissue around the microparticles within the nucleus pulposus can impart a certain physical stability to the interior of the spinal disk and/or to exterior portion of the annulus fibrosis. Later testing after the sealant (i.e., the biocompatible alloplastic implant) has matured (e.g., been incorporated into the host tissue through, for example, formation of permanent scar tissue around the microparticles of the implant) can yield an increase in the pressure gradient of the nucleus pulposus. Also, a slight increase in spinal disk space height may be achieved in proportion to the amount of the biocompatible alloplastic implant instilled which may vary from spinal disk to spinal disk, but which in a representative embodiment does not exceed about 3 to 4 cubic centimeters (ccs) and, typically, is within a range of about 0.5 to 1.5 ccs. During injection, it is advantageous to release pressure on the syringe plunger when the tip of the needle is within about 3-5 mm from the outer surface of the disk during removal of the needle from the disk.

Regarding maturation of the microparticles, which in a representative embodiment may comprise PMMA spherical beads, as a result of the size and physical stability of the PMMA beads, they cannot be phagocytised or lysed. In order to isolate the foreign body, the animal body can only fibrotically wall off the foreign bodies in the form of scar tissue. Such a process takes place with almost any foreign body which cannot be destroyed by the animal body. Prior to or substantially commensurate in time with installation of the biocompatible alloplastic implant and any removal of a part of the spinal disk (if applicable), the annular fibers that are attached to the vertebra end plates above and below can be minimally resected to allow punctate bleeding to occur from, for example, the edges of the end plate.

It can be advantageous for the microparticles used according to an embodiment of the present invention to have a smooth surface and be free from corners and edges, such that the microparticles don't have sharp transitions on their surfaces. In addition they may not have peaks of any kind or tapered projections. According to one implementation, the surface does not have pores. In another implementation, the surfaces may comprise pores. Although smooth, and especially spherical particles can be advantageous, in some embodiments, non-smooth microparticles of with corners or peaks or the like may still be used in the present spinal disk treatment application.

Fully polymerised PMMA is histocompatible and can be incorporated in the human body without harmful toxic or carcinogenic reactions so that it can be considered as chemically and physically inert and biocompatible. For these reasons, PMMA polymers have already been used for manufacturing implants such as bone cement for the plastic covering of bone defects in the face and in the cranium, or as in a total hip or total knee arthroplasty. The polymer is also being used for manufacturing artificial teeth, as artificial heart valves and for manufacturing intra-ocular lenses and dialysis membranes. In some embodiments, a biocompatible alloplastic implant may include PMMA having less than 3% MMA monomer, the MMA molecule being non-soluble in water. PMMA having less than 3% MMA monomer is non-toxic and biocompatible. In some embodiments, endotoxin levels of the biocompatible alloplastic implant may be less than 0.06 EU/ml. In some embodiments, the biocompatible alloplastic implant may have a pH value of between 6.5 and 7.5. In certain implementations, the biocompatible alloplastic implant may have a pH value of between 7.0 and 7.5.

The mixing ratio of the components of the suspending agent can be chosen according to the needs, and in particular according to the size of the syringe used for the injection. For example, the viscosity of a suspending agent comprising hyaluronic acid can be controlled by altering the molecular weight, the concentration, or the amount of cross-linking of hyaluronic acid in the solution. For the application or injection of the microparticles used according to an embodiment of the present invention, the microparticles can be suspended or slurried in a fluid inert medium. In one particular implementation, a ratio of two volume parts of the suspending agent and one volume part of the microparticles or polymer microparticles is chosen.

Representative embodiments of a biocompatible alloplastic implant can be processed by the following steps: (i)

hydrating hyaluronic acid in PBS, (ii) adding PMMA particles, (iii) stirring the composition, (iv) loading the implant into a syringe, and (v) sterilizing via autoclave. Autoclaving may be performed at temperatures of about 120° C. Steam autoclave sterilization does not damage PMMA microspheres having a glass transition temperature above the autoclaving temperature. The biocompatible alloplastic implant can be terminally stabilized, meaning that autoclave sterilization can be performed on whole syringes already filled with the implant in the barrel, eliminating the need for aseptic material processing and loading.

Additionally, medical kits may be produced containing elements necessary for treating and/or repairing tendons and ligaments with the tissue-promoting implant. Such a kit may include a quantity of the implant, and a delivery device, such as a syringe or other applicator. One or more surgical tools used in conventional spinal disk access and repair surgery may optionally also be advantageously provided in such kits.

In one preferred embodiment, a biocompatible alloplastic implant may include a suspending agent having sterile PBS and linear, implant grade, endotoxin-free, non-sterile hyaluronic acid having a molecular weight of greater than 1.6 M Da, a purity of greater than 95%, a moisture percentage of between 8% and 15% and a concentration in PBS of between 1.0% and 3.0%. The biocompatible alloplastic implant can also include non-sterile, endotoxin-free, cross-linked PMMA microspheres having a glass transition temperature greater than 130° C., an average diameter between 40 and 110 microns, a purity of greater than 95%, a concentration of PMMA within the biocompatible alloplastic implant of between 25% and 50%, and a conformance within the above lower and upper specification limits of greater than 80%. The biocompatible alloplastic implant may be used with a 1 ml long glass pre-fillable syringe having a standard medical grade hypodermic needle, in which the needle is at least 3 inches in length and 20-guage or smaller. The syringe may have a standard luer female connector for needle connection. The biocompatible alloplastic implant may have an endotoxin levels of less than 0.06 EU/ml, a pH of between 6.5 and 7.5, and a shelf life of greater than 12 months when stored between 2° and 8° C. The filled syringe may be steam sterilized and have a sterility assurance level of $10^{-6}$.

In another preferred embodiment, a biocompatible alloplastic implant may include a suspending agent having sterile PBS and linear, implant grade, endotoxin-free, non-sterile hyaluronic acid having a molecular weight of greater than 2.8 M Da, a purity of greater than 95%, a moisture percentage of between 8% and 15% and a concentration in PBS of between 1.6% and 2.4%. The biocompatible alloplastic implant can also include non-sterile, endotoxin-free, cross-linked PMMA microspheres having a glass transition temperature greater than 130° C., an average diameter between 50 and 100 microns, a purity of greater than 95%, a concentration of PMMA within the biocompatible alloplastic implant of between 38% and 48%, and a conformance within the above lower and upper specification limits of greater than 90%. The biocompatible alloplastic implant may be used with a 1 ml long glass pre-fillable syringe having a standard medical grade hypodermic needle, in which the needle is at least 6 inches in length and 21-guage or smaller. The syringe may have a standard luer female connector for needle connection. The biocompatible alloplastic implant may have an endotoxin levels of less than 0.06 EU/ml, a pH of between 670 and 7.5, and a shelf life of greater than 18 months when stored between 2° and 8° C. or room temperature. The filled syringe may be steam sterilized and have a sterility assurance level of $10^{-6}$.

Experimental Data

Experiments were performed using a biocompatible alloplastic implant including HTL Biosciences sodium hyaluronate (the sodium salt of hyaluronic acid) and Syringa Lab Supplies Ganzpearl GM-5003 crosslinked PMMA Poly(methyl methacrylate) microspheres. The sodium hyaluronate had an intrinsic viscosity of 2.92 m$^3$/kg at 25° C. and an average molecular weight of 3.1 M da. The PMMA microspheres had a diameter range from 53 to 106 microns, with a mean diameter of 66.15 microns, a median diameter of 63.51 microns, and a standard deviation of 10.02 microns. Less than 1% of the microspheres had diameters outside of the 50-100 micron range. The specific gravity of the PMMA microspheres was 1.19.

Extrusion Force Testing

On Nov. 11, 2015 extrusion force testing was performed for various compositions of a biocompatible alloplastic implant having hyaluronic acid and PMMA microspheres with the specifications described above. When forming the implant, the sodium hyaluronate was hydrated and reconstituted with sterile PBS. The PMMA beads were washed in 1N NaOH, rinsed in sterile water for injection (SWFI), and dried, but not sterilized. In the experiment, 1 cc BD-Hypak syringes were used to extrude the implant through 22-gauge, 6 inch RELI spinal needles. Prior to testing, the syringes were autoclaved. The syringes underwent terminal sterilization at 120° C. for 15 minutes of exposure under 15-81 psi with a slow ramp up and Air-Over-Pressure exhaust. Three formulations were tested: Formula A having a concentration of hyaluronic acid in PBS of 2.0% and including 40.5% (w/w) PMMA; Formula B having a concentration of hyaluronic acid in PBS of 2.0% and including 42.5% (w/w) PMMA; and Formula C having a concentration of hyaluronic acid in PBS of 2.2% and including 42.5% (w/w) PMMA. Each formulation was tested at syringe travel rates of 1.5 inches per minute and 2.5 inches per minute, using three different syringes for each travel rate. The extrusion force testing was performed at room temperature on a Mark-10 Force Stand with a calibrated 50 lb load cell. The formulations tested and the mean extrusion forces measured are summarized in Table 1 below.

TABLE 1

| PRODUCT CONCENTRATION | MEAN EXTRUSION FORCE @ 1.5"/min | MEAN EXTRUSION FORCE @ 2.5"/min |
| --- | --- | --- |
| Formula A: 2.0% HA base, 40.5% PMMA | 27.6N | 29.0N |
| Formula B: 2.0% HA base, 42.5% PMMA | 28.8N | 30.8N |
| Formula C: 2.2% HA base, 42.5% PMMA | 32.0N** 1-Syringe Failed | All (3) syringes failed |

Sheep Study

A study was performed by the North American Science Association (NAMSA) using a test article including a composition of 1.2% (w/w) hyaluronic acid, 40.5% (w/w) cross-linked PMMA microspheres, and 58.3% (w/w) buffered PBS. The hyaluronic acid had an average molecular weight of 3.0 M Da. The PBS had a pH of 7.1 and an osmolarity of 300 mOs/L. The PMMA microspheres had an average diameter of 53 to 106 microns. The glass transition temperature of the PMMA beads was 135° C., and the specific gravity was 1.19. The PMMA microspheres also contained a linking agent. The rotational viscosity of this formulation was measured at 89,000 centipoise with a shear rate of 4 sec$^{-1}$ and an extrusion force of 29.0 N using one technique, and at 190,000 centipoise with a shear rate of 1 sec$^{-1}$ using another technique.

The purpose of the study was to evaluate the local tissue response to the biocompatible alloplastic implant implanted in the intervertebral discs of sheep. The following parameters were measured: cleft formation with a loss of nucleus pulposus, disintegration of nucleus pulposus matrix, clones of chondrocyte-like cells, lobulation, extrusion of nucleus pulposus into vertebral bodies, inflammation, neovascularization, and nerve ingrowth.

The spinal columns of the tested animals were provided to NAMSA with location marker designation. Animal 13R had a wire marker located on the transverse process of the third lumbar vertebrae, per Euthanasia and Tissue Collection form. Animal 88Y had a wire marker located on the transverse process of the third lumbar vertebrae, per Euthanasia and Tissue Collection form. Animal 35Y had a wire marker located on the transverse process of the third lumbar vertebrae, per Euthanasia and Tissue Collection form. Animal 13Y had a wire marker located on the transverse process of the second lumbar vertebrae, per Euthanasia and Tissue Collection form. Orientation and disc location was determined from the wire markers for each animal.

The spinal columns for each animal were submerged in 10% neutral buffered formalin and shipped to NAMSA. After arrival at NAMSA, the lumbar vertebrae were cut along a transverse plane to create functional spinal units (i.e., caudal half of cranial vertebra, intervertebral disc and cranial half of caudal vertebra). The lumbar functional spinal units (FSUs) were fixed in 10% neutral buffered formalin to ensure adequate fixation. Coronal sections of the intervertebral discs were collected using a bone saw, decalcified, processed and embedded in paraffin blocks. A minimum of three tissue sections (4-5 μm thick) were prepared of each intervertebral disc to capture the area of the nucleus pulposus and one tissue section of the overlying spinal cord and spinal canal. These sections were stained with hematoxylin and eosin.

Over a three month interval, the intervertebral discs of four animals from Group 1 were evaluated for findings associated with the test article and the microscopic appearance of uninjured and injured intervertebral disc cytoarchitecture which included the nucleus pulposus and anulus fibrosus. The presence, distribution and alterations, such as encapsulation, in the test article were evaluated. The following findings in the nucleus pulposus matrix of uninjured and injured intervertebral discs were evaluated: cleft formation with a loss of nucleus pulposus, disintegration of nucleus pulposus matrix, clones of chondrocyte-like cells, lobulation, extrusion of nucleus pulposus into vertebral bodies, inflammation, neovascularization, and nerve ingrowth.

The test article was nonstaining microspheres that were found in the intervertebral disc sections labeled L1-L2 and L3-L4 for all four animals (FIG. 1). FIG. 1 shows a test article within the nucleus polposus of intervertebral disc sections L1-L2 of test animal 13Y. There was no tissue reaction (including encapsulation) to the presence of the microspheres in any of the eight treated intervertebral discs. The microspheres were generally in clusters and mainly in the nucleus pulposus, although a few were between bands of the AF (e.g., L1-L2 of 13Y). The microspheres were occasionally organized in clusters and surrounded by a thin layer of basophilic matrix material.

Figure 2:
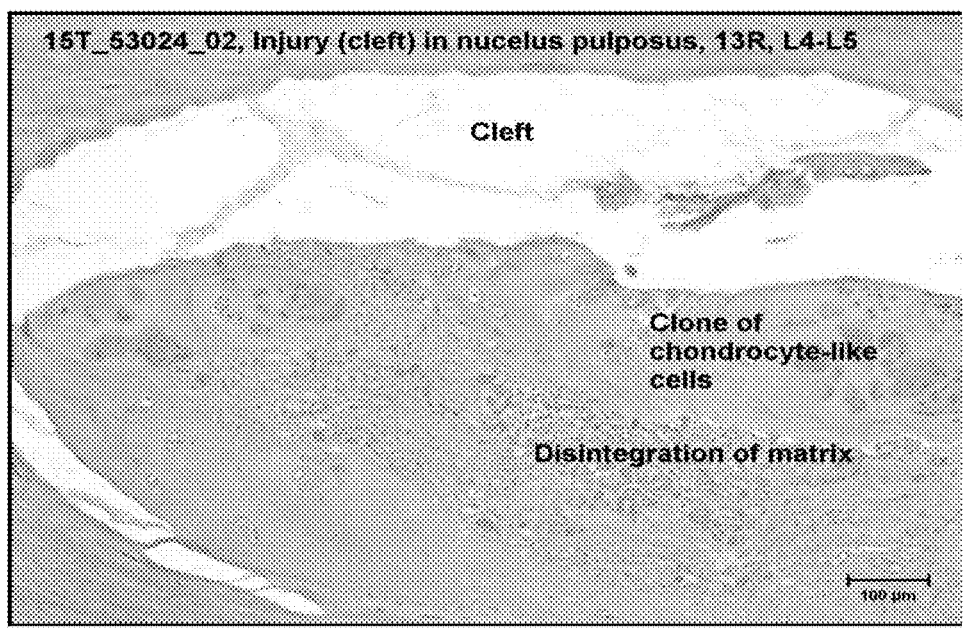
FIG. 2 depicts a cleft in a nucleus pulposus of intervertebral disc sections L4-L5 of a test animal 13R.

Evidence of injury (i.e., cleft in nucleus pulposus, usually large) was apparent microscopically in the intervertebral disc sections labeled L2-L3 and L4-L5 for all four animals (FIG. 2), except in several injured intervertebral discs (L2-L3 of 35Y; L2-L3 of 13R; L1-L2 of 13Y; L3-L4 of 13Y and L3-L4 of 88Y). FIG. 2 shoes a cleft in a nucleus pulposus of intervertebral disc sections L4-L5 of test animal 13R resulting from injury. The nucleus polposus has degenerative changes that include clones of chondrocyte-like cells and disintegration of the matrix. The lack of microscopic evidence of injury may have been the result of the plane of tissue section.

The microscopic findings in the injured intervertebral discs (with or without treatment) were present in uninjured intervertebral discs (L5-L6 and L6-L7) and were considered nonspecific degenerative findings in intervertebral discs. The microscopic findings included disintegration of the nucleus pulposus matrix, clefts, lobulation of the nucleus pulposus matrix and the presence of chondrocyte-like cells forming clones.

There was no apparent narrowing of the intervertebral disc space in the histologic sections. Focal cranial extrusion of the nucleus pulposus into the adjacent vertebral body was present at L3-L4 of 88Y and caudal extrusion of the nucleus pulposus into the adjacent vertebral body of L6-L7 intervertebral disc of 88Y. This finding was considered a nonspecific degenerative condition. Inflammation, neovascularization and nerve ingrowth were not apparent in the intervertebral disc sections.

After the three month interval, there was no tissue reaction to the test article in the intervertebral discs of sheep that were injured by an annular tear. Information regarding the test animals is provided in Table 2 below:

TABLE 2

| Test Animal | Intervertebral Disc Section Data |
|---|---|
| Animal: 35Y | L1-L2 (Injured, Treated): (1) Large central cleft in the NP, (2) Lobulation of the NP matrix with multifocal clones of chondrocyte-like cells, (3) Presence of test article in the NP without reaction. L2-L3 (Injured, Untreated): (1) Normal NP cytoarchitecture with slight disintegration of NP matrix, (2) No test article. L3-L4 (Injured, Treated): (1) Central cleft in NP, (2) Lobulation of the NP matrix with multiple clones of chondrocyte-like cells, (3) Presence of test article in peripheral NP. L4-L5 (Injured, Untreated): (1) Large central cleft in the NP, (2) Slight lobulation of the NP matrix with multiple clones of chondrocyte-like cells, (3) No test article. L5-L6 (Uninjured, Untreated): (1) Normal NP cytoarchitecture with slight disintegration of NP matrix and a cleft, (2) No test article. L6-L7 (Uninjured, Untreated): (1) Large central cleft in the NP, (2) Lobulation of the NP matrix with multifocal clones of chondrocyte-like cells, (3) Disintegration of NP matrix, (4) No test article. |
| Animal: 13R | L1-L2 (Injured, Treated): (1) Large central cleft in the NP, (2) Lobulation of the NP matrix with multifocal clones of chondrocyte-like cells, (3) Presence of test article in the NP without reaction. L2-L3 (Injured, Untreated): (1) Normal NP cytoarchitecture with slight disintegration of NP matrix, (2) No test article. L3-L4 (Injured, Treated): (1) Central cleft in NP, (2) Lobulation of the NP matrix with multiple clones of chondrocyte-like cells, (3) Presence of test article in central NP without reaction. L4-L5 (Injured, Untreated): (1) Focal central cleft in the NP, (2) Focal lobulation of the NP matrix with a few clones of chondrocyte-like cells, (3) Slight and focal disintegration of NP matrix (3) No test article. |

TABLE 2-continued

| Test Animal | Intervertebral Disc Section Data |
|---|---|
| | L5-L6 (Uninjured, Untreated): (1) Distortion of NP cytoarchitecture with slight disintegration of NP matrix and a cleft, (2) No test article.<br>L6-L7 (Uninjured, Untreated): (1) Central disintegration of NP matrix, (2) Focal lobulation of the NP matrix with multifocal clones of chondrocyte-like cells, (3) No test article |
| Animal: 13Y | L1-L2 (Injured, Treated): (1) Normal NP cytoarchitecture with slight disintegration of NP matrix, (2) Presence of test article in NP with slight disintegration of NP matrix, (3) Presence of test article in AF.<br>L2-L3 (Injured, Untreated): (1) Central cleft in NP, (2) Aggregates of NP in AF (3) No test article.<br>L3-L4 (Injured, Treated): (1) Normal NP cytoarchitecture with slight disintegration of NP matrix, (2) Slight and focal disruption of NP matrix, (3) Test article was present in the AF and a slight amount was present in the NP.<br>L4-L5 (Injured, Untreated): (1) Focal peripheral cleft in the NP, (2) Slight and focal disintegration of NP matrix (3) No test article.<br>L5-L6 (Uninjured, Untreated): (1) Multifocal disintegration of NP matrix with clefts, (2) Aggregates of NP in AF, (3) Multifocal disruption of AF matrix (4) No test article.<br>L6-L7 (Uninjured, Untreated): (1) Normal NP cytoarchitecture with slight disintegration of NP matrix, (2) No test article. |
| Animal: 88Y | L1-L2 (Injured, Treated): (1) Large central cleft in the NP, (2) Lobulation of the NP matrix with multifocal clones of chondrocyte-like cells, (3) Slight disintegration of NP matrix, (4) Presence of test article in NP without reaction.<br>L2-L3 (Injured, Untreated): (1) Slight cleft, (2) Slight lobulation, (3) Slight NP matrix disintegration, (4) No test article.<br>L3-L4 (Injured, Treated): (1) Slight lobulation of the NP matrix, (2) Slight NP matrix disintegration (3) Focal cranial extrusion of NP into adjacent vertebral body, (4) A slight amount of test article was present in the NP.<br>L4-L5 (Injured, Untreated): (1) Slight cleft formation, (2) Slight lobulation of NP matrix with chondrocyte-like aggregation, (3) Slight disintegration of NP matrix, (4) No test article.<br>L5-L6 (Uninjured, Untreated): (1) Central cleft in the NP, (2) Lobulation of the NP matrix with multifocal clones of chondrocyte-like cells, (3) No test article.<br>L6-L7 (Uninjured, Untreated): (1) Central cleft in the NP, (2) Lobulation of the NP matrix with multifocal clones of chondrocyte-like cells, (3) Slight NP matrix disruption, (4) Slight, multifocal disintegration of AF, (5) Focal caudal extrusion of NP into adjacent vertebral body, (6) No test article. |

Representative Methods and Uses

It will be appreciated that the invention has a variety of aspects. In accordance with some of these aspects, a biocompatible alloplastic implant can be utilized for annular welding or sealing of a spinal disk defect, such as a ruptured spinal disk. The biocompatible alloplastic implant can be inserted into a ruptured spinal disk, filling a portion of the nucleus pulposus or annulus fibrosis and providing a seal. In one implementation, the biocompatible alloplastic implant is inserted into a central region of the ruptured spinal disk. Insertion of the biocompatible alloplastic implant into the ruptured spinal disk can attenuate a risk for recurrent spinal disk herniation and restore at least a portion of a structural integrity or shock absorbing capacity of the spinal disk.

In some aspects of the invention, a biocompatible alloplastic implant containing hyaluronic acid is inserted into a disk. In certain embodiments, hyaluronic acid acts as a carrier or a suspending agent for a plurality of microparticles previously described herein. The biocompatible alloplastic implant containing hyaluronic acid may be inserted with a syringe and needle, via flexible catheters of variable length and diameter, such as, for example, standard percutaneous needles and standard catheter tips known in the industry, or with the aid of an injection syringe, such as a syringe having a 3 or 4" 18-gauge needle. In representative embodiments, the size of the needle can range from 14-gauge to 26-gauge. In some embodiments, the size of the needle can range from 20-gauge to 24-gauge. In some embodiments, the needle comprises a pencil point needle.

Hyaluronic acid, acting as a carrier for the microparticles, can be advantageous in treating tears or fissures on the annulus fibrosus or other defects that form in the spinal disk. Hyaluronic acid can work to correct defects both before herniation in order to prevent future complications and after herniation to repair and reinforce the spinal disk. Additionally, hyaluronic acid can fortify the structural integrity of a spinal disk. Due to the hydrophilic nature of hyaluronic acid, a biocompatible alloplastic implant including microparticles, such as PMMA beads, and a suspending agent including hyaluronic acid can draw water into a spinal disk from the endplates of adjacent vertebrae. This attribute of hyaluronic acid can help maintain disk height in a treated spinal disk. Furthermore, the hydrophilic nature of hyaluronic acid can also prevent extrusion through the temporary needle perforation in the annulus fibrosis that is created during injection. A biocompatible alloplastic implant including microparticles and a hyaluronic acid suspending agent can bind with water molecules after insertion to increase the viscosity of and volume of the implant within the disc. The increased viscosity and volume can prevent extrusion through the needle perforation. Thus, the binding of water molecules with the hyaluronic acid suspending agent can act as an internal curing process to prevent extrusion from the disc as well as repairing and reinforcing the disk. Repair and fortification through treatment with a biocompatible alloplastic implant including a hyaluronic acid suspending agent may prevent patients from having to undergo repeat surgeries to correct back issues. Treatment can improve stability and flexibility of the spine, as well the shock absorption properties of the treated spinal disk.

Hyaluronic acid can also be advantageous in treating spinal disks that are collapsing or weakened. It can fortify those disks and correct defects. Thus, a biocompatible alloplastic implant including a hyaluronic acid suspending agent may alleviate back pain and prevent further complications from collapsing or weakened disks.

Embodiments of implants including a hyaluronic acid suspending agent may also be beneficial in treating disks adjacent to a planned fusion. These disks may be under a greater risk of developing herniation, tears or defects. A fusion may also act to worsen any preexisting defects in adjacent spinal disks. A hyaluronic acid suspending agent containing microparticles can be used to treat preexisting tears and to fortify the structural integrity of an adjacent disk before or after a planned fusion in order to prevent further complications.

A method of treating a spinal disk according to the present invention can comprise identifying a defect in a spinal disk and inserting an alloplastic bulking agent into the spinal disk to thereby treat the defect, wherein the alloplastic bulking agent comprises a plurality of microparticles and a suspending agent comprising hyaluronic acid. The identifying of a defect can comprise, for example, identifying a defect through a scope. In typical implementations, the identifying of a defect can comprise identifying a focal outpouching comprising a displacement of nucleus pulposus within a partially torn or thinned annulus fibrosis of the spinal disk, can comprise identifying an extrusion comprising displaced nucleus pulposus which remains in continuity with an interior of the spinal disk through a rent in an annulus fibrosis of the spinal disk, or can comprise identifying a sequestration comprising displaced nucleus pulposus which does not remain in continuity with an interior of the spinal disk.

The inserting can comprise inserting an alloplastic bulking agent into the spinal disk while viewing at least a part of the spinal disk through a scope. The scope can comprise a video fluoroscope, and the inserting can be fluoroscopically guided. In one implementation, the alloplastic bulking agent can be impregnated with a water soluble radiopaque dye to facilitate visualization during the inserting of the alloplastic bulking agent into the spinal disk. The radiopaque dye can comprise barium. In a typical implementation, the inserting can comprise inserting about 3 or 4 cubic centimeters (ccs) or less of the alloplastic bulking agent into a nucleus pulposus of the spinal disk, and in certain implementations the inserting comprises inserting about 0.5 to 1.5 cubic centimeters (ccs) of the alloplastic bulking agent into the nucleus pulposus of the spinal disk.

The inserting may be followed by a height of the spinal disk being increased, wherein the increase in height is proportional to an amount of the alloplastic bulking agent inserted into the spinal disk. In accordance with one aspect of the present invention, the inserting may be followed by a structural integrity of the spinal disk being improved, compared to a structural integrity of the spinal disk before the inserting. For example, a stability of the annulus fibrosis of the spinal disk may be improved relative to a stability of the annulus fibrosis before the inserting, whereby a biomechanical property of a motion segment of the spinal disk is improved compared to biomechanical property of the motion segment before the inserting.

When the spinal disk is juxtapositioned in proximity to at least one of an upper vertebra and a lower vertebra, at least one aperture can be formed in an endplate of one or both of the upper vertebra and the lower vertebra. Typically, the spinal disk is juxtapositioned between an upper vertebra and a lower vertebra, and a plurality of apertures are formed in an endplate or endplates of at least one of the upper vertebra and the lower vertebra. The aperture or apertures can be formed using a needle, which may already be present in the spinal disk during an ongoing procedure such as, for example, a diskography procedure.

In representative implementations of the methods disclosed herein, the defect comprises a spinal annular defect. For instance, the defect can comprise an internal disk derangement. Insertion of the alloplastic bulking agent into the spinal disk can cause a seal to be formed in and around the spinal annular defect. This seal can create a more stable motion segment of the spinal disk compared to a motion segment of the spinal disk before the inserting, by for example imparting increased stability to the spinal disk relative to a stability of the spinal disk before the inserting.

The inserting can be performed during a diskography procedure, and the defect can comprise at least one annular rent. During the diskography procedure, the identifying can comprise an initial visualization of the at least one rent followed by the inserting being performed during the same diskography procedure. In accordance with one implementation of the inventive methods disclosed herein, the diskography procedure comprises a provocative diskography procedure wherein the identifying comprises an initial visualization of the at least one rent and wherein the inserting is performed during the same provocative diskography procedure.

According to another implementation, the diskography procedure can be performed percutaneously through one of a posterior, posterolateral, lateral, anterior or anterolateral approach to the spinal disk.

In other implementations, the inserting can be performed during an open procedure, and can comprise inserting the alloplastic bulking agent using a syringe and needle into the spinal disk in one of a laminotomy, laminectomy, hemilaminotomy and hemilaminectomy open procedure.

Another method of the present invention that can be performed on a spinal disk includes delivering a bulking material comprising a plurality of microparticles and a suspending agent comprising hyaluronic acid into a spinal disk. The delivering can be preceded by inserting an injection device into the spinal disk, and the bulking material can be delivered though the injection device and into the spinal disk. When the spinal disk is positioned in proximity to at least one of an upper vertebra endplate and a lower vertebra endplate, the method can comprise forming one or more apertures or perforations in at least one of the upper vertebra endplate and the lower vertebra endplate.

The delivering of a bulking material can comprise delivering a bulking material into a nucleus pulposus of the spinal disk, such as a central or non-perimeter region of the spinal disk. The delivering can be preceded by detecting a condition in the spinal disk, and the bulking material can be delivered into the spinal disk to treat the condition. Furthermore, the microparticles can be shaped as, for example, microspheres, and can be uniformly distributed in a suspending agent comprising hyaluronic acid. Moreover, the detecting of a condition can comprise detecting a displacement of inner disk material within a partially torn or thinned annulus of the spinal disk, and the delivering can comprise delivering an amount on the order of about 3 to 4 cubic centimeters (ccs) or less of the bulking material into the spinal disk.

The efficacy of the techniques described above may be further improved by maintaining the patient at a reduced activity level for several weeks following implantation of the biocompatible alloplastic implant. With a reduced level of activity, the biocompatible alloplastic implant may remain in a disc until the annulus can heal in approximately 3-4 weeks. The perforation caused by the injection needle decreases in size over time due to healing in the mid to outer annulus. Accordingly, the greatest risk of extrusion occurs during the first 2-3 weeks. Thus, the techniques described above may include a further step of reducing patient activity for 2-3 or 3-4 weeks following implantation of the biocompatible alloplastic implant.

It may also be noted that the techniques described herein can be used to advantageous effect for treating household pets such as dogs and cats. In these cases, vertebral fusions and similar procedures are often cost prohibitive, so any lower cost techniques for disk repair would be beneficial.

The above-described embodiments have been provided by way of example, and the present invention is not limited to these examples. Multiple variations and modifications to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the present invention is not intended to be limited by the disclosed embodiments.

What is claimed is:

1. An implant agent comprising a plurality of microparticles suspended in a solution containing hyaluronic acid, for use in repairing and/or improving structural integrity of spinal disks, wherein the implant agent is without any gelling or setting agents that cause the material to polymerize, gel, or otherwise harden in place after injection through an annulus, and wherein the microparticles comprise cross-linked polymethymethacrylate (PMMA) microparticles having a glass transition temperature of at least 120 degrees C. such that the microparticles are more stable to thermal exposure during autoclaving.

2. The implant agent of claim 1, wherein the solution containing hyaluronic acid comprises cross-linked hyaluronic acid.

3. The implant agent of claim 1, wherein the PMMA microparticles have an average diameter between 15 microns to 250 microns.

4. The implant agent of claim 1, wherein the concentration of hyaluronic acid in the solution is between 1.0% and 3.0%.

5. The implant agent of claim 1, wherein the concentration of hyaluronic acid in the solution is between 1.6% and 2.4%.

6. The implant agent of claim 1, wherein the molecular weight of hyaluronic acid in the agent is greater than 1.6 M Da.

7. The implant agent of claim 1, wherein the molecular weight of hyaluronic acid in the agent is greater than 2.8 M Da.

8. The implant agent of claim 1, wherein the concentration of PMMA microparticles in the agent is between 25% and 50%.

9. The implant agent of claim 1, wherein the concentration of PMMA microparticles in the agent is between 38% and 48%.

10. The implant agent of claim 1, wherein the solution has a viscosity between 50,000 and 200,000 centipoise.

* * * * *